United States Patent
Tomiyama et al.

[11] Patent Number: 5,990,158
[45] Date of Patent: Nov. 23, 1999

[54] CARBOXYLIC ACID DERIVATIVES, METHOD OF MANUFACTURING THE SAME AND THERAPEUTIC AGENTS CONTAINING THESE COMPOUNDS

[75] Inventors: Tsuyoshi Tomiyama; Akira Tomiyama, both of Nagano-ken; Takashi Yanagisawa, Kousyoku; Atsushi Noda, Nagano-ken; Yoshinori Kobayashi, Kousyoku, all of Japan

[73] Assignee: Kotobuki Seiyaku Co., Ltd., Nagano-ken, Japan

[21] Appl. No.: 08/963,195

[22] Filed: Nov. 3, 1997

[30] Foreign Application Priority Data

Nov. 1, 1996 [JP] Japan .................................. 8-291737

[51] Int. Cl.$^6$ .......................... A01N 43/26; A61K 31/335
[52] U.S. Cl. .......................... 514/467; 514/449; 514/461; 514/463; 564/123; 564/199; 549/450; 549/451; 549/452
[58] Field of Search .............................. 554/68; 564/305, 564/123, 199; 562/433, 443; 549/296, 321, 450, 451, 452; 514/449, 461, 469, 467

[56] References Cited

FOREIGN PATENT DOCUMENTS

95/22966 8/1995 WIPO .
WO95/22966 8/1995 WIPO .

OTHER PUBLICATIONS

Casreact Abstr. of JP–04/149170, 1995.
Organic Chemistry, 9th ed., pp. 183 & 313, 1995.
M.R. Gowravaram, et al. "Inhibition of Matrix Metalloproteinases by Hydroxamates Containing Heteroatom–Based Modifications of the $P_1'$ Group", J. Med. Chem., 1995, 38, pp. 2570–2581.
B.E. Tomczuk, et al., "Hydroxamate Inhibitors of the Matrix Metallo–Proteinases (MMPs) Containing Novel $P_1'$ Heteroatom Based Modifications", Biorganic & Medicinal Chem. Letters, vol. 5, No. 4, pp. 343–348 (1995).

*Primary Examiner*—Deborah D Carr
*Attorney, Agent, or Firm*—Sherman and Shalloway

[57] ABSTRACT

New therapeutic agents of carboxylic acid derivatives are disclosed, which are represented by the compounds of the following formula (I) or its pharmaceutically acceptable salts,

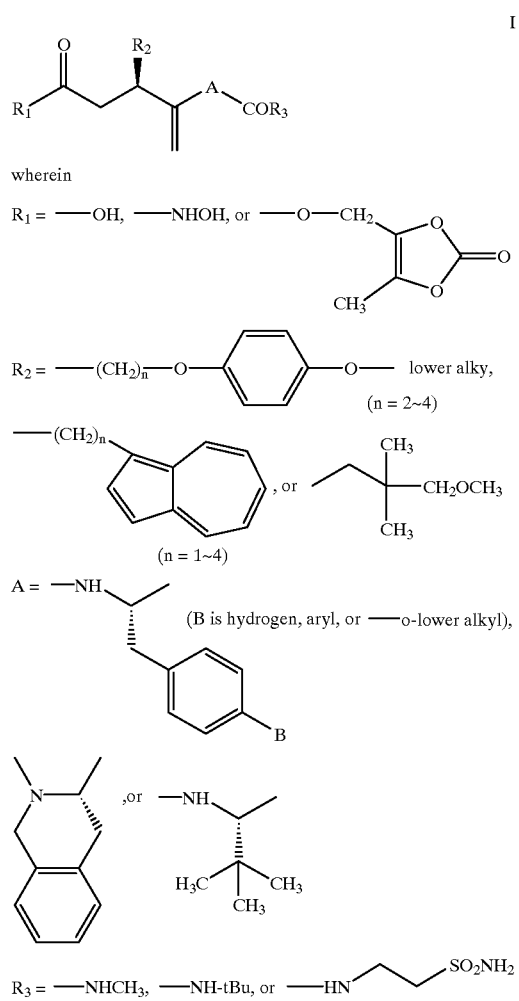

These compounds are useful as a matrix metalloproteinases (MMPs) inhibitors.

3 Claims, No Drawings

CARBOXYLIC ACID DERIVATIVES, METHOD OF MANUFACTURING THE SAME AND THERAPEUTIC AGENTS CONTAINING THESE COMPOUNDS

BACKGROUND OF THE INVENTION

1. Field of the Invention

This invention relates to carboxylic acids and the derivative compounds thereof which have a Matrix Metalloproteinases (hereinafter shortened to MMPs) inhibitory function or the pharmaceutically acceptable salts thereof and the production method thereof; and further relates to a medicine containing said carboxylic acids, derivative compounds thereof or the salts thereof.

2. Description of the Prior Art

The MMPs are zinc dependent, calcium requiring enzymes that are involved in the degradation of extra cellular matrix. Under normal physiological conditions, the expression of the constitutive MMPs is low, and regulated by naturally occurring inhibitors termed TIMPs (tissue inhibitor of metalloproteinases). However, under pathological conditions such as rheumatoid and osteoarthritis, MMPs expression in cartilage is disregulated and results in over expression of MMPs which are not controlled by constitutive TIMPs. The level of the MMPs is high with enzymic activity and exceeding the level of the TIMPs. This condition leads to a loss of proteoglycan and collagen (J. Trzaskos, et al., Acta. Onthopaedica Scandinavia, 66, 150 (1995)).

In addition, MMPs inhibitors are effective on treatment for corneal ulceration and tumor progression (R. P. Beckett, et al., D.D.T., 1, 16 (1996)), and MMPs are playing important role in the pathogenesis of arteriosclerosis and restenosis after percutaneous transluminal coronary angioplasty (PTCA) (C. M. Dollery, et al., Circ. Res., 77, 863 (1995)). It is therapeutically useful to control the increased MMPs by MMPs inhibitors under these pathological conditions. Recently, a review of MMPs inhibitors has been published (R. P. Beckett, et al., D.D.T., 1, 16 (1996)).

3. Problems to be Solved by the Invention

Though many reported MMPs inhibitors had excellent in vitro activity, these compounds had poor oral bioavailabilities. For example, the compounds had been administered by intrapleural administration (Drug News & Perspectives, 8 (4), 247, (1995)) or eye drops (Drug of the Future, 18, 1101 (1993)).

The object of the present invention is the provision of pharmaceutical compositions useful as MMPs inhibitors being capable of oral administration and a production method thereof.

DETAILED DESCRIPTION OF THE INVENTION

The present invention provides a new carboxylic acid derivative compound of general formula (I):

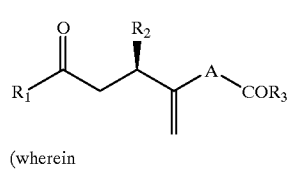

(wherein $R_1 = $ —OH, —NHOH, or —O—$CH_2$—(dioxolone with CH$_3$), $R_2 = $ —$(CH_2)_n$—O—C$_6$H$_4$—O—lower alkyl, (n = 2~4)

—$(CH_2)_n$-azulenyl, or —C(CH$_3$)$_2$—CH$_2$OCH$_3$ (n = 1~4)

A = —NH—CH(B-C$_6$H$_4$)— (B is hydrogen, aryl, or —o-lower alkyl), tetrahydroisoquinoline-N-yl, or —NH—C(CH$_3$)$_2$-H$_3$C-CH$_3$ $R_3 = $ —NHCH$_3$, —NH-tBu, or —HN—CH$_2$CH$_2$—SO$_2$NH$_2$ )

and its salts capable of being used for medical treatment. The lower alkyl mentioned in general formula (I) represents the straight or branched $C_1$–$C_5$ alkyl.

The compound of general formula (I) can be obtained as follows:

(1) In the case of $R_1$ is —OH and $R_3$ is —NHCH$_3$ or —NH—tBu in the compounds of general formula (I), it is prepared by the following reactions.

$R_4O$-C(=O)-CH$_2$-CH($R_2$)-C(=O)-OH (II) $\xrightarrow{\text{HA—COR}_3 \text{ (III)}}{\text{DEPC}}$ $R_4O$-C(=O)-CH$_2$-CH($R_2$)-C(=O)-A-COR$_3$ (IV) $\xrightarrow{\text{TFA/CH}_2\text{Cl}_2}$

HO-C(=O)-CH$_2$-CH($R_2$)-C(=O)-A-COR$_3$ (V)

(wherein $R_2$, $R_3$, $R_4$, and A are the same as mentioned above.)

(2) In the case of $R_1$ is —OH and $R_3$ is —NH(CH$_2$)$_2$SO$_2$NH$_2$ in the compounds of general formula (I), it is prepared by the following reactions.

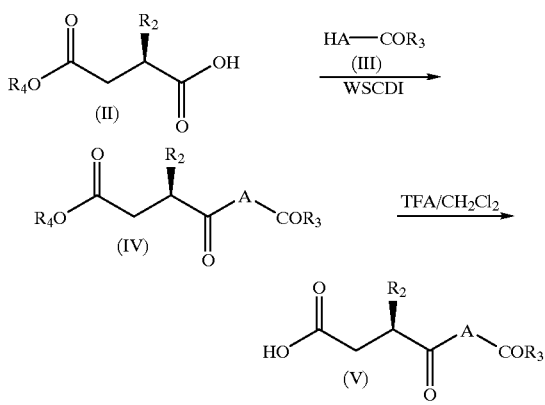

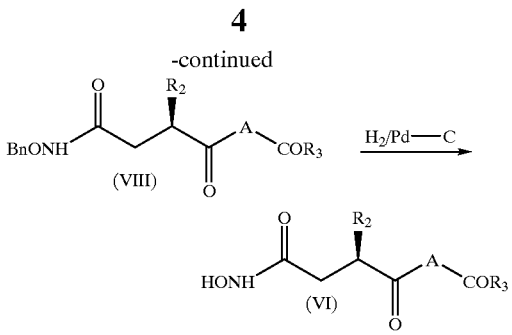

(wherein $R_2$, $R_3$, $R_4$, and A are the same as mentioned above.)

Estercarboxylic acid (II) is reacted with amine (III) using coupling reagents to yield esteramide (IV). This reaction is called Yamada coupling which use diphenylphosphorylazide (DPPA) or diethylphosphoryl cyanide (DEPC) as coupling reagents in the presence of triethylamine in DMF (S. Yamade, et al., J. Am. Chem. Soc., 94. 6203 (1972)). In addition, dicyclohexyl-carbodiimide (DCC), carbonyldiimidazole (CDI), or 1-(3-dimethylaminopropyl)-3-ethylcarbodiimide. HCl salt (WSCDI) et cetera are used as coupling reagents.

Carboxylic acid amide (V) is obtained by hydrolysis of ester amide (IV) using trifluoracetic acid (TFA), mineral acid (HCl, $H_2SO_4$), or alkali-metal hydroxide (NaOH, KOH or LiOH).

(3) In the case of $R_1$ is NHOH in the compounds of the general formula (I), it is prepared by the following reactions.

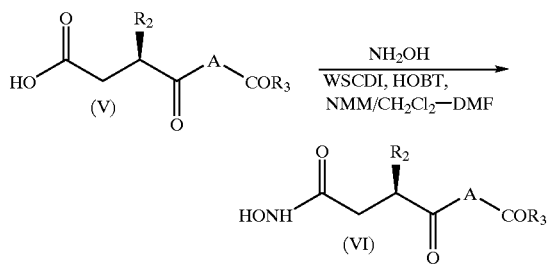

(wherein $R_2$, $R_3$, and A are the same as mentioned above.)

Carboxylicacidamide (V) is reacted with hydroxylamine in the presence of coupling reagents (DPPA, DEPC, DCC, or WSCDI) to yield hydroxamic acid amide (VI). (HOBT: 1-Hydroxybenzo-triazole; NMM: N-Methylmorpholine).

Hydroxamic acid amide (VI) is also obtained by production of 0-benzylhydroxamic acid amide (VIII) using o-benzylhydroxylamine ($NH_2OBn$) instead of hydroxylamine and subsequently debenzylation.

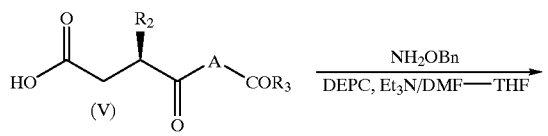

The compound (VI) is also obtained from a reaction of hydroxylamine with activated ester (IX) which was derived from the compound (V) using N-hydroxysuccinimide (S. B. Singh, Tetra. Lett. 36, 2009 (1995)).

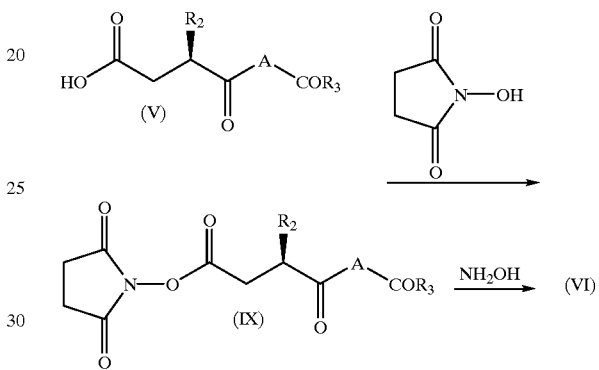

(wherein $R_2$, $R_3$ and A are the same as mentioned above.)

(4) In case of $R_1$ is (5-methyl-2-oxo-1,3-dioxoren-4-yl) methylen oxy group in the compounds of the general formula (I), it is prepared by the following reactions.

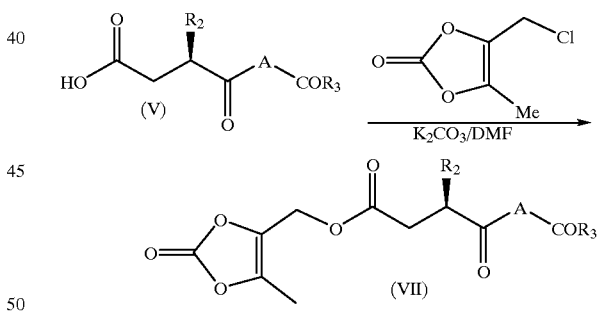

(wherein $R_2$, $R_3$, and A are the same as mentioned above.)

According to method of H. M. Fischler, et al. (Tetra Lett., 1701 (1972)), the compound using above reaction is obtained by halogenation of dimethylvinylcarbonate (XV) which was prepared by acyroin and phosgen (F. Sakamoto, et al., Chem. Pharm. Bull., 32, 224 (1984)).

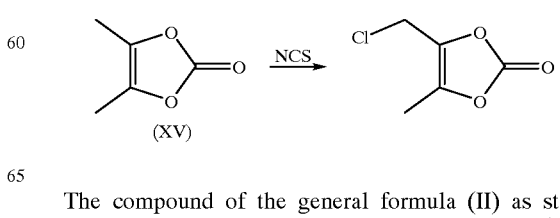

The compound of the general formula (II) as starting material is obtained by Evans' asymmetic alkylation (Evans,

D. A., J.A.C.S., 104, 1737 (1982)).

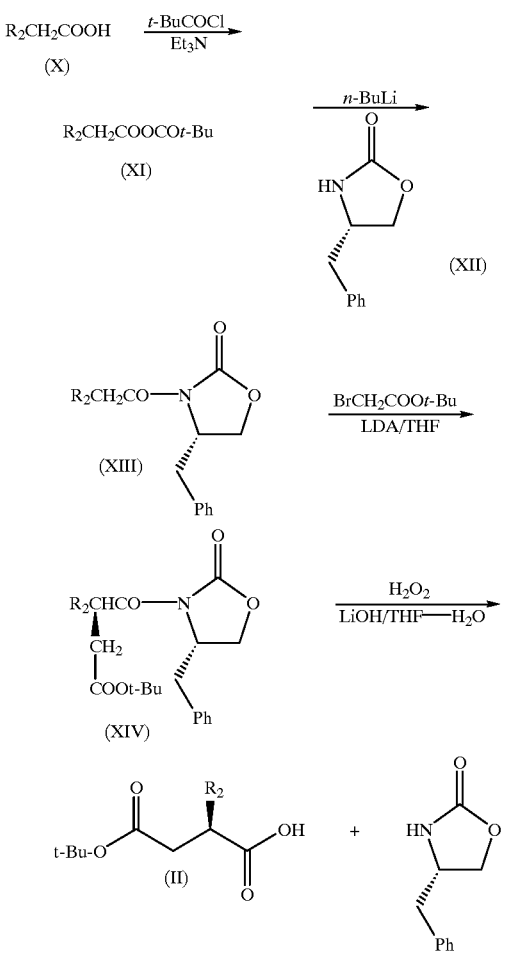

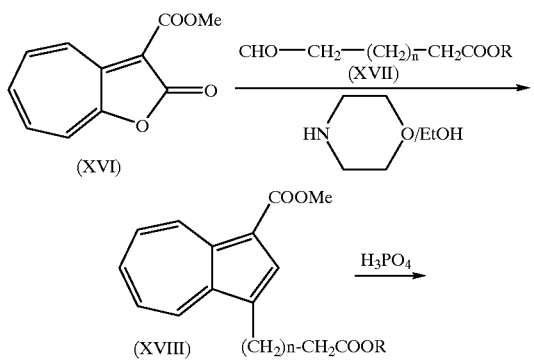

The compound (X) is reacted with (S)-(-)-4-benzyl-2-oxazolidine (XII) via mixed anhydride (XI) to yield the compound (XIII). Then an alkylation is performed to give the compound (XIV), and the auxiliary is removed to yield the compound (II).

Preparation of the compound (X) being above starting material is as follows.

(1) In the case of $R_2$ is alkylazulene group.

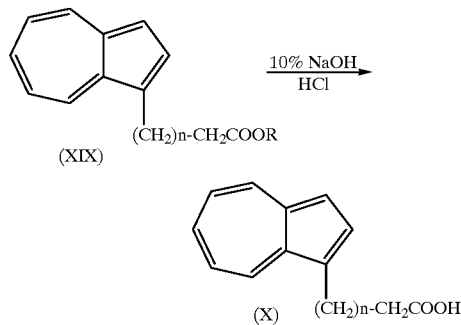

The oxazolanone (XVI) is reacted with aldehyde (XVII) to yield azulene diester (XVIII) by the enamine method (T. Yanagisawa, et al., Chem. Pharm. Bull., 36 (1988)). The compound (XVIII) is converted to azulene monoester (XIX) by demethoxycarbonylation, and it is subsequently hydrolyzed to yield azulene carboxylic acid (X).

The aldehyde (XVII) is obtained by following reactions. The lactone (XX) is converted to the compound (XXI) by acid-mediated ring-opening reaction in alcohol (ROH). Subsequently, the aldehyde (XVII) is obtained by PCC (pyridinium chlorochromate) oxidation.

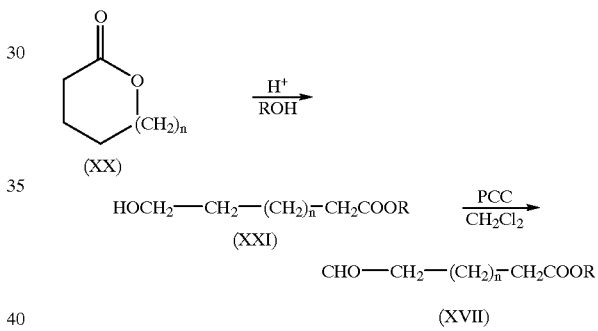

(2) In the case of $R_2$ is p-alkoxyphenolic ether group.

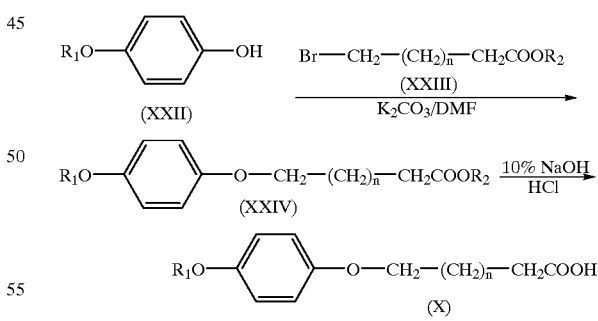

p-Alkoxyphenol (XXII) is converted to phenoxyester (XXIV), then it is subsequently hydrolyzed to yield p-substituted phenoxy carboxylic acid (X).

(3) In case of $R_2$ is —$CH_2$—$C(CH_3)_2(CH_2OCH_3)$ group.

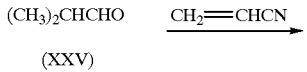

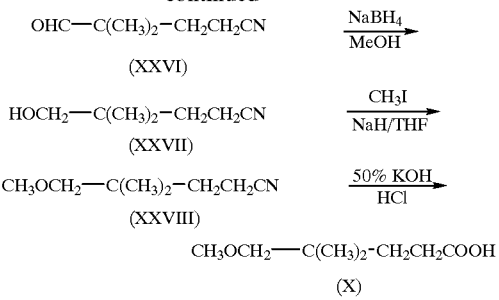

Isobutylaldehyde (XXV) is reacted with acrylonitrile to yield aldehyde (XXVI), and it is converted to alcohol (XXVII) by NaBH$_4$. Subsequently, it is reaction CH$_3$I to yield methyl derivative (XXVIII), and carboxylic acid (X) is obtained by hydrolysis.

The compounds of the general formula (I) are exemplified as follows.

1. N-[(2R)-2-(1'-Carboxymethyl)-3-(azulene-1-yl)propionyl]-L-phenylanine N-Methylamide (Compound 1).
2. N-[(2R)-2-(1'-Carboxymethyl)-4-(azulene-1-yl)butyroyl]-L-phenylalanine N-Methylamide (Compound 2).
3. (2S)-2-[(2R)-2-(1'-Carboxymethyl)-4-(azulene-1-yl)butyroyl)amino-3-(4-methoxy)phenylpropanoylmethylamide (Compound 3).
4. N-[(2R)-2-(1'-Carboxymethyl)-4-(azulene-1-yl)butyroyl]-L-tert-leucine N-Methylamide (Compound 4).
5. N-[(2R)-2-(1'-Carboxymethyl)-5-(azulene-1-yl)pentanoyl]-L-phenylalanine N-Methylamide (Compound 5).
6. (2S)-2-[(2R)-2-(1'-Carboxymethyl)-4-(azulene-1-yl)butyroyl]amino-3-(4-ethoxy)phenylpropanoyl methylamide (Compound 6).
7. N-[(2R)-2-(1'-Carboxymethyl)-6-(azulene-1-yl)hexanoyl]-L-phenylalanine N-Methylamide (Compound 7).
8. N-[(2R)-2-(1'-Carboxymethyl)-4-[(4-methoxyphenyl)oxy]butyroyl]-L-phenylalanine N-Methylamide (Compound 8).
9. N-[(2R)-2-(1'-Carboxymethyl)-4-[(4-ethoxyphenyl)oxy]butyroyl]-L-phenylalanine N-Methylamide (Compound 9).
10. N-[(2R)-2-(1'-Carboxymethyl)-5-[(4-methoxyphenyl)oxy]pentanoyl]-L-phenylanine N-Methylamide (Compound 10).
11. N-((2R)-2-(1'-Carboxymethyl)-5-[(4-methoxyphenyl)oxy]pentanoyl-L-phenylalanine N-tert-Butylamide (Compound 11).
12. 2-[[N-(2R)-2-(1'-Carboxymethyl)-5-[(4-methoxyphenyl)oxy]pentanoyl]-L-phenylalanyl]amino-ethanesulfonamid (Compound 12).
13. N-[(2R)-2-(1'-Carboxymethyl)-5-[(4-ethoxyphenyl)oxy]pentanoyl]-L-phenylalanine N-Methylamide (Compound 13).
14. N-[(2R)-2-(1'-Carboxymethyl)-6-[(4-methoxyphenyl)oxy]hexanoyl-L-phenylananine N-Methylamide (Compound 14).
15. N-((2R)-2-(1'-Carboxymethyl)-6-[(4-ethoxyphenyl)oxy]hexanoyl]-L-phenylananine N-Methylamide (Compound 15).
16. N-[(2R)-2-(1'-Carboxymethyl)-6-[(4-allyloxyphenyl)oxy]hexanoyl]-L-phenylananine N-Methylamide (Compound 16).
17. (2S)-2-[(2R)-2-(1'-Carboxymethyl)-4-[(4-methoxyphenyl)-oxy]butyroyl]amino-3-(4-methoxy)phenylpropanoylmethylamide (Compound 17).
18. (2S)-2-[(2R)-2-(1'-Carboxymethyl)-5-[(4-methoxyphenyl)oxy)]pentanoyl]amino-3-(4-methoxy)phenylpropanoylmethylamide (Compound 18).
19. (2S)-2-[(2R)-2-(1'Carboxymethyl)-5-[(methoxyphenyl)oxy]pentanoyl]amino-3-(4-methoxy)phenylpropanoyl-tert-butylamide (Compound 19).
20. 2-[(2S)-2-[(2R)-2-(1'Carboxymethyl)-5-[(4-(methoxyphenyl)-oxy]pentanoyl]amino-3-(4-methoxy)phenylpropanoyl]amino-ethanesulfonamide (Compound 20).
21. (2S)-2-[(2R)-2-(1'-Carboxymethyl)-6-[(4-methoxyphenyl)-oxy]hexanoyl]amino-3-(4-methoxy)phenylpropanoylmethylamide (Compound 21).
22. (2S)-2-[(2R)-2-(1'-Carboxymethyl)-5-[(4-methoxyphenyl)-oxy]pentanoyl]amino-3-(4-ethoxy)phenylpropanoylmethylamide (Compound 22).
23. (2S)-2-[(2R)-2-(1'-Carboxymethyl)-6-[(4-methoxyphenyl)oxy]hexanoyl]amino-3-(4-ethoxy)phenylpropanoylmethylamide (Compound 23).
24. N-[(2R)-2-(1'-Carboxymethyl)-5-[(4-methoxyphenyl)oxy]pentanoyl]-L-tert-leucine N-Methylamide (Compound 24).
25. N-[(2R)-2-(1'-Carboxymethyl)-5-[(4-methoxyphenyl)oxy]pentanoyl]-L-tert-leucine N-tert-Butylamide (Compound 25).
26. 2-[[N-((2R)-2-(1'-Carboxymethyl)-5-[(4-methoxyphenyl)oxy]pentanoyl]-L-tert-leucyl]amino-ethanesulfonamide (Compound 26).
27. N-[(2R)-2-(1'-Carboxymethyl)-5-[(4-methoxyphenyl)oxy]pentanoyl]-L-tetrahydroisoquinoline N-Methylamide (Compound 27).
28. N-[(2R)-2-(1'-Carboxymethyl)-4,4-dimethyl-5-methoxy-pentanoyl]-L-phenylalanine N-methylamide (Compound 28).
29. (2S)-2-[(2R)-2-(1'-Carboxymethyl)-4,4-dimethyl-5-methoxypentanoyl]amino-3-(4-methoxy)phenylpropanolmethylamide (Compound 29).
30. N-[(2R)-2-(1'-Carboxymethyl)-4,4-dimethyl-5-methoxypentanoyl]-L-tert-leucine N-methylamide (Compound 30).
31. N-[(2R)-2-(2'-Hydroxyamino-2'-oxo-ethyl)-3-(azulene-1-yl)-propionyl]-L-phenylanine N-Methylamide (Compound 31).
32. N-[(2R)-2-(2'-Hydroxyamino-2'-oxo-ethyl)-4-(azulene-1-yl)-butyloyl]-L-phenylanine N-Methylamide (Compound 32).
33. (2S)-2-[(2R)-2-(2'-Hydroxyamino-2'-oxo-ethyl)-4-(azulene-1-yl)butyloyl]amino-3-(4-methoxy)phenylpropanoylmethylamide (Compound 33).
34. N-[(2R)-2-(2'-Hydroxyamino-2'-oxo-ethyl)-4-(azulene-1-yl)-butyloyl]-L-tert-leucine N-Methylamide (Compound 34).
35. N-[(2R)-2-(2'-Hydroxyamino-2'-oxo-ethyl)-5-(azulene-1-yl)-pentanoyl]-L-phenylalanine N-Methylamide (Compound 35).
36. (2S)-2-[(2R)-2-(2'-Hydroxyamino-2'-oxo-ethyl)-4-(azulene-1-yl)butyloyl]amino-3-(4-ethoxy)phenylpropanoylmethylamide (Compound 36).
37. N-[(2R)-2-(2'-Hydroxyamino-2'-oxo-ethyl)-6-(azulene-1-yl)-hexanoyl]-L-phenylalanine N-Methylamide (Compound 37).
38. N-[(2R)-2-(2'-Hydroxyamino-2'-oxo-ethyl)-4-[(4-methoxyphenyl)oxy]butyloyl]-L-phenylalanine N-Methylamide (Compound 38).

39. N-[(2R)-2-(2'-Hydroxyamino-2'-oxo-ethyl)-4-[(4-ethoxy-phenyl)oxy]butyloyl]-L-phenylalanine N-Methylamide (Compound 39).
40. N-[(2R)-2-(2'-Hydroxyamino-2'-oxo-ethyl)-5-[(4-methoxyphenyl)oxy]pentanoyl]-L-phenylalanine N-Methylamide (Compound 40).
41. N-[(2R)-2-(2'-Hydroxyamino-2'-oxo-ethyl)-5-[(4-methoxyphenyl)oxy]pentanoyl]-L-phenylalanine N-tert-Butylamide (Compound 41).
42. 2-[N-[(2R)-2-(2'-Hydroxyamino-2'-oxo-ethyl)-5-[(4-methoxyphenyl)oxy]pentanoyl]-L-phenylalanyl]amino-ethanesulfonamide (Compound 42).
43. N-[(2R)-2-(2'-Hydroxyamino-2'-oxo-ethyl)-5-[(4-ethoxy-phenyl)oxy]pentanoyl]-L-phenylalanine N-Methylamide (Compound 43).
44. N-[(2R)-2-(2'-Hydroxyamino-2'-oxo-ethyl)-6-[(4-methoxyphenyl)oxy]hexanoyl]-L-phenylalanine N-Methylamide (Compound 44).
45. N-[(2R)-2-(2'-Hydroxyamino-2'-oxo-ethyl)-6-[(4-ethoxy-phenyl)oxy]hexanoyl]-L-phenylalanine N-Methylamide (Compound 45).
46. N-[(2R)-2-(2'-Hydroxyamino-2'-oxo-ethyl)-6-[(4-allyloxy-phenyl)oxy]hexanoyl]-L-phenylalanine N-Methylamide (Compound 46).
47. (2S)-2-[(2R)-2-(2'-Hydroxyamino-2'-oxo-ethyl)-4-[(4-methoxyphenyl)oxy]-butyloyl]amino-3-(4-methoxy)phenylpropanoylmethylamide (Compound 47).
48. (2S)-2-[(2R)-2-(2'-Hydroxyamino-2'-oxo-ethyl)-5-[(4-methoxyphenyl)oxy]-pentanoyl]amino-3-(4-methoxy)phenyl- propanoylmethylamide (Compound 48).
49. (2S)-2-[(2R)-2-(2'-Hydroxyamino-2'-oxo-ethyl)-5-[(4-methoxyphenyl)oxy]-pentanoyl]amino-3-(4-methoxy)phenyl-propanoyl-tert-butylamide (Compound 49).
50. 2-[(2S)-2-[(2R)-2-(2'-Hydroxyamino-2'-oxo-ethyl)-5-[(4-methoxyphenyl)oxy]-pentanoyl]amino-3-(4-methoxy)phenylpropanoyl]amino-ethanesulfonamide (Compound 50).
51. (2S)-2-[(2R)-2-(2'-Hydroxyamino-2'-oxo-ethyl)-6-[(4-methoxyphenyl)oxy]-hexanoyl]amino-3-(4-methoxy)phenylpropanoylmethylamide (Compound 51).
52. (2S)-2-[(2R)-2-(2'-Hydroxyamino-2'-oxo-ethyl)-5-[(4-methoxyphenyl)oxy]-pentanoyl]amino-3-(4-ethoxy)phenylpropanoylmethylamide (Compound 52).
53. (2S)-2-[(2R)-2-(2'-Hydroxyamino-2'-oxo-ethyl)-6-[(4-methoxyphenyl)oxy]-hexanoyl]amino-3-(4-ethoxy)phenylpropanoylmethylamide (Compound 53).
54. N-[(2R)-2-(2'-Hydroxyamino-2'-oxo-ethyl)-5-[(4-methoxyphenyl)oxy]-pentanoyl]-L-tert-leucine N-Methylamide (Compound 54).
55. N-[(2R)-2-(2'-Hydroxyamino-2'-oxo-ethyl)-5-[(4-methoxyphenyl)oxy]-pentanoyl]-L-tert-leucine N-tert-Butylamide (Compound 55).
56. 2-[N-[(2R)-2-(2'-Hydroxyamino-2'-oxo-ethyl)-5-[(4-methoxyphenyl)oxy]pentanoyl]-L-tert-leucyl]amino-ethanesulfonamide (Compound 56).
57. N-[(2R)-2-(2'-Hydroxyamino-2'-oxo-ethyl)-5-[(4-methoxyphenyl)oxy]pentanoyl]-L-tetrahydroisoquinoline N-Methylamide (Compound 57).
58. N-[(2R)-2-(2'-Hydroxyamino-2'-oxo-ethyl)-4,4-dimethyl-5-methoxy-pentanoyl]-L-phenylalanine N-Methylamide (Compound 58).
59. (2S)-2-[(2R)-2-(2'-Hydroxyamino-2'-oxo-ethyl)-4,4-dimethyl-5-methoxy-pentanoyl]amino-3-(4-methoxy)phenylpropanoyl- methylamide (Compound 59).
60. N-[(2R)-2-(2'-Hydroxyamino-2'-oxo-ethyl)-4,4-dimethyl-5-methoxy-pentanoyl]-L-tert-leucine N-Methylamide (Compound 60).
61. N-[(2R)-2-[2'-(5-Methyl-2-oxo-1,3-dioxolen-4-yl)methylene-oxy-2'-oxo-ethyl]-5-[4-methoxyphenyl)oxy]pentanoyl]-L- phenylalanine N-Methylamide (Compound 61).
62. N-[(2R)-2-[2'-(5-Methyl-2-oxo-1,3-dioxolen-4-yl)methylene-oxy-2'-oxo-ethyl]-5-[4-ethoxyphenyl)oxy]pentanoyl]-L-phenylalanine N-Methylamide (Compound 62).
63. (2S)-2-[(2R)-2-(2'-(5-Methyl-2-oxo-1,3-dioxolen-4-yl)-methylene-oxy-2'-oxo-ethyl]-5-[(4-methoxyphenyl)oxy]-pentanoyl]amino-3-(4-methoxy)phenylpropanoylmethylamide (Compound 63).
64. (2S)-2-[(2R)-2-(2'-(5-Methyl-2-oxo-1,3-dioxolen-4-yl)-methylene-oxy-2'-oxo-ethyl]-6-[(4-methoxyphenyl)oxy]-hexanoyl]amino-3-(4-methoxy)phenylpropanoylmethylamide (Compound 64).

The carboxylic acid derivatives in this invention are useful as pharmaceutical compositions used to treat and/or prevent disease related to destruction of extra cellular matrix induced by MMPs. They can be administered orally in the form of tablets, capsules, granules and syrups, and also can be administered intravenously. An effective dosage of the compounds is from 10 to 1000 mg once to several times a day for adults, though it may be adjusted depending on age and symptoms.

PHARMACOLOGICAL EXPERIMENT

The compound of the general formula (I) in the invention is a potent inhibitor of MMPs. A pharmacological experiment is described as follows.

Experiment 1: MMP-1 (type I collagenase) inhibitory activities.

Inhibition of MMP-1 (type I collagenase) activities were estimated by enzyme assay using human fibroblasts derived MMP-1 (Yagai Co. Ltd.) and type I collagenase activity assay kit (Yagai Co. Ltd., E. D. Harris, Jr., et al., Method Enzymol., 82, 423 (1982)). MMP-1 (0.01 U/ml), test compound ($10^{-10}$ ~$10^{-5}$ M concentrations), and fluorescein isothiocyanate (FITC)-labeled type I collagen (50 μg) were incubated in 500 μl of 0.05M Tris-HCl buffer (pH 7.5) containing 200 mM NaCl and 5 mM $CaCl_2$ at 37° C. for 4 h. The reaction was stopped by 0.05M Tris-HCl buffer (pH 9.5) containing 200 mM NaCl, 50 mM o-fenantroline and ethanol, and the mixture was centrifuged at 15000 g for 10 min and fluorescence intensity (EX 495 nm, EM 520 nm) of the resulting supernatant was measured. The degradation percent of substrate was calculated by comparison with a fluorescence intensity of heat denatured substrate as 100%. Inhibition of MMP-1 activity was expressed as an $IC_{50}$ value which was the concentration of test compound necessary to produce 50% inhibition of collagen type I degradation induced MMP-1. The inhibition activity ($IC_{50}$, M) of the compounds of this Experiment is from $10^{-5}$ to $10^{-8}$.

Experiment 2: MMP-2 (gelatinase A) and MMP-9 (gelatinase B) inhibitory activities.

Pro MMP-2 was obtained from culture medium separated from human pro-MMP-2 cDNA tranfected COS-1 cells. It was activated by 1 mM (p-aminophenyl)mercury acetic acid, and MMP-9, derived human fibrosarcome, was purchased from Yagai Co. Ltd. Inhibition of both enzyme activities were estimated by enzyme assay using type IV collagenase activity assay kit (Yagai Co. Ltd., Biswaz, C. et al., J. Cell.Biochem., 28, 39 (1984)). MMP-2 or MMP-9 (0.01 U/ml), test compound (several concentrations), and FITC-labeled type IV collagen (derived bovine placenta, 25 μg) were incubated in 100 μl of 0.05M Tris - HCl buffer (pH 7.5) containing 200 mM NaCl and 5 mM $CaCl_2$ at 42° C. for 4 h. Inhibitory activity of compound was evaluated by same as that of MMP-1 assay. Unchanged type IV collagen was precipitated by centrifugation, and the degradation percent of substrate was calculated by comparison with a fluorescence intensity of heat denatured substrate as 100%. Inhibition of enzyme activity was expressed as an $IC_{50}$ value which was the concentration of test compound necessary to produce 50% inhibition of collagen type IV degradation by enzyme. The results are described in Table 1.

TABLE 1

Inhibition activity of C50, nM)

| Comp. | MMP-2 | MMP-9 | Comp. | MMP-2 | MMP-9 |
|---|---|---|---|---|---|
| 2 | 390 | 1300 | 36 | 180 | 24 |
| 3 | 240 | 280 | 37 | 2700 | 2900 |
| 4 | 1000 | 300 | 38 | 13 | 2.3 |
| 5 | >10000(45.3%) | 2800 | 39 | 8.8 | 1.4 |
| 6 | 1000 | 360 | 40 | 1.0 | 0.18 |
| 7 | >10000 | 3000 | 41 | 3.1 | 0.13 |
| 8 | 160 | 35 | 42 | 0.36 | 0.051 |
| 9 | 49 | 39 | 43 | 0.97 | 0.14 |
| 10 | 50 | 5.1 | 44 | 1.3 | 0.41 |
| 11 | 100 | 14 | 45 | 4.0 | 0.72 |
| 12 | 21 | 3 | 46 | 250 | 160 |
| 13 | 18 | 13 | 47 | 11 | 1.2 |
| 14 | 160 | 120 | 48 | 9.0 | 0.15 |
| 15 | 61 | 420 | 49 | 26 | 0.42 |
| 16 | 180 | 1000 | 50 | 0.45 | 0.052 |
| 17 | 46 | 13 | 51 | 2.5 | 0.28 |
| 18 | 250 | 5.4 | 52 | 1.0 | 0.12 |
| 19 | 76 | 13 | 53 | 3.2 | 0.32 |
| 20 | 16 | 2.9 | 54 | 5.6 | 0.11 |
| 21 | 160 | 52 | 55 | 21 | 0.23 |
| 22 | 140 | 9.5 | 56 | 2.3 | 0.26 |
| 23 | 200 | 51 | 57 | 37 | 23 |
| 24 | 140 | 7.2 | 58 | >10000(39.8%) | 2200 |
| 25 | 200 | 28 | 59 | 6800 | 1500 |
| 26 | 48 | 6.5 | 60 | >10000(26.6%) | 6800 |
| 27 | >10000(28.7%) | 1500 | 61 | 1000 | 110 |
| 32 | 3200 | 400 | 62 | 500 | 120 |
| 33 | 160 | 18 | 63 | 1600 | 140 |
| 34 | 760 | 52 | 64 | 2300 | 980 |
| 35 | 1300 | 2500 | | | |

EFFECTIVENESS OF THE INVENTION

The compounds of the present invention are novel, potent and oral active MMPs inhibitors.

REFERENTIAL EXAMPLE

Referential example 1

Synthesis of azulene-1-propionic acid (a) Synthesis of 3-methoxycarbonyl-propylaldehyde A solution of δ-varerolactone 14.9 g in $H_2SO_4$ (5 mL) and MeOH (200 mL) was heated under reflux for 17 h. After cooling at −10° C., $NaHCO_3$ (1.5 g) was added to the reaction mixture and stirred for 10 min. The insoluble portion was removed by filtration. After removal of the solvent in vacuo from the filtrate, the residue was dissolved in $CH_2Cl_2$ (300 mL). Molecular sieves (49 g) and pyridium chlorochromate (PCC) (49 g) were added to the mixture at 0° C., and the mixture was stirred for 1 h at room temperature. The insoluble portion was removed by filtration through Celite, the filtrate was evaporated to give the aldehyde (15 g). ($M^+$=114).

(b) Synthesis of 1-methoxycarbonyl-3-(3-methoxycarbonylpropionyl) azulene

3-Methoxycarbonyl-propylaldehyde (7.0 g) which was prepared by referential example 1(a) was dissolved in EtOH (100 mL), then morpholine (5.4 mL) and oxaazulanone (8.3 g) were added, and the mixture was refluxed for 16 h. The reaction mixture was concentrated in vacuo. After addition of ethyl acetate, the ethyl acetate layer washed with brine, dried ($Na_2SO_4$), filtered, and concentrated. The resulting product was purified by silica gel column chromatography ($SiO_2$, 250 g) using EtOAc:n-hexane (1:2). The object compound was obtained as a violet oil (9.9 g). MS (m/e): 292($M^+$), 199 (BP). IR ($cm^{-1}$): 2938, 1731, 1686, 1443, 1308.

$^1$H-NMR ($CDCL_3$): 2.78 (2H,t), 3.37 (2H,t), 3.68 (3H,s), 3.95 (3H,s), 7.42 (1H,t), 7.49 (1H,t), 7.77 (1H,t), 8.23 (1H,s), 8.43 (1H,d), 9.58 (1H,d).

(c) Synthesis of azulene-1-propionic acid methylester

1-Methoxycarbonyl-3-(3-methoxycarbonylpropionyl) azulene (9.9 g) which was prepared by referential example 1(b) was added to 100% phosphoric acid (50 mL), and the mixture was stirred for 20 min at 110° C. After cooling at room temperature, the mixture was poured into ice water. The reaction mixture was extracted with ethyl acetate (50 mL×3), then the ethyl acetate layer was washed with brine, dried ($Na_2SO_4$), filtered, and concentrated. The resulting product was purified by silica gel column chromatography ($SiO_2$, 250 g) using EtOAc:n-hexane (1:10). The object compound was obtained as a blue oil (6.5 g).

MS (m/e): 214 ($M^+$), 141 (BP). IR ($cm^{-1}$):1731, 1575, 1434, 1395.

$^1$H-NMR ($CDCl_3$): 2.77 (2H,t), 3.42 (2H,t), 3.67 (3H,s), 7.08 (1H,t), 7.12 (1H,t), 7.32 (1H,d), 7.55 (1H,t), 7.78 (1H,d), 8.26 (1H,d), 8.29 (1H,d).

(d) Synthesis of azulene-1-propionic acid

Azulene-1-propionic acid methyl ester (6.5 g) which was prepared by referential example 1(c), was dissolved in MeOH (70 mL), and it was added to 10% NaOH (30 mL) and the mixture was stirred for 2 h at room temperature. After the mixture was concentrated in vacuo, the pH value of the resulting residue was adjusted to 3.0 by 10% HCl. The reaction mixture was extracted with ethyl acetate (50 mL×3). The ethyl acetate layer was washed with brine and dried ($Na_2SO_4$), filtered, and concentrated in vacuo. The resulting product was purified by silica gel column chromatography ($SiO_2$, 200 g) using EtOAc:n-hexane (1:4). The object compound was obtained as a blue crystal (4.2 g).

MP (°C.):113~115. MS (m/e): 200 ($M^+$), 141 (BP). IR ($cm^{-1}$),: 3022, 2914, 1689, 1434, 1413.

$^1$H-NMR ($CDCl_3$): 2.82 (2H,t), 3.43 (2H,t), 7.10 (1H,t) 7.13 (1H,t), 7.33 (1H,d), 7.56 (1H,t), 7.80 (1H,d), 8.27 (1H,d), 8.31 (1H,d).

Referential Example 2

Synthesis of [6-(4-methoxyphenyl)oxy]-hexanoic acid.

(a) Synthesis of ethyl[6-(4-methoxyphenyl)oxy]hexanate

A mixture of p-methoxyphenol (5 g), $K_2CO_3$ (8.35 g) and ethyl 6-bromohexanate (10.7 mL) in DMF (80 mL) was heated overnight at 60° C. $H_2O$ was added to it, and the mixture was extracted with ether. The ether layer washed with $H_2O$, brine and dried ($Na_2SO_4$), filtered, and concentrated in vacuo. The resulting product was purified by silica gel column chromatography. The object compound was obtained. (10.7 g).

MS (m/e): 266 ($M^+$), 143, 124 (BP), 109, 95, 69, 55. IR ($cm^{-1}$),: 2932, 1731, 1509, 1230, 1182, 1035, 822, 750.

$^1$H-NMR ($CDCl_3$: δ1.25 (3H, t, Et), 1.49 (2H,q,—$CH_2$—), 1.70 (2H, quint,—$CH_2$—), 1.78 (2H, q,—$CH_2$—), 2.33 (2H,t,—$CH_2$—), 3.76 (3H,s, —$OCH_3$), 3.90 (2H,t,—$OCH_2$—), 4.13 (2H,q,Et), 6.82 (4H,s,aromatic).

(b) Synthesis of [6-(4-methoxyphenyl)oxy]hexanoic acid

Ethyl-[6-(4-methoxyphenyl)oxy] hexanate (10.7 g) which was prepared by referential example 2(a) was dissolved in EtOH (40 mL), then it was added to 10% KOH (30 mL), and the mixture was stirred for 1 h at room temperature. After the mixture was concentrated in vacuo, the resulting residue was treated with chloroform. The cloroform layer was washed with brine, dried ($Na_2SO_4$), filtered, and concentrated in vacuo. The object compound was obtained (8.51 g).

MS (m/e): 238 ($M^+$), 124 (BP), 109, 95, 69, 55. IR ($cm^{-1}$),: 2932, 2638, 1716, 1509, 1473, 1428, 1305, 1245, 1221, 1203, 1176, 1035, 1005, 825, 747.

$^1$H-NMR ($CDCl_3$): $\delta$1.53 (2H,m,—$CH_2$—), 1.71 (2H, quint,—$CH_2$—), 1.78 (2H,quint,—$CH_2$—), 2.40 (2H,t,—$CH_2$—), 3.77 (3H,s,—$OCH_3$), 3.91 (2H,t,—$OCH_2$—), 6.83 (4H,s,aromatic), 11.20 (1H,brs,—$CO_2H$).

Referential Example 3

Synthesis of 4—dimethyl-5—methoxy-pentanoic acid (a) Synthesis of 4—dimethyl-4—formylbutyronitrile 50% NaOH (10 mL) was added to a solution of isobutylaldehyde (25 g) and acrylonitrile (73.5 g) at 0° C. and the mixture was stirred for 3 h at 25–35° C. The reaction mixture was poured into water (150 mL) and extracted with ethyl acetate (50 mL×3). The ethyl acetate layer was washed with brine and dried ($Na_2SO_4$), filtered, and concentrated. The resulting product was distilled to afford the object compound (29 g). BP: 90~100° C./2 mmHg.

MS(m/e): 125 ($M^+$), 96, 55 (BP). IR ($cm^{-1}$),: 2962, 2872, 1722, 1470, 880.

$^1$H-NMR ($CDCl_3$): $\delta$1.13 (6H,s,$(CH_3)_2$), 1.89 (2H,t,$CH_2$), 2.32 (2H,t,$CH_2$), 9.44 (1H,s,CHO).

(b) Synthesis of 4-hydroxymethyl-4-dimethyl-butyronitrile

4-Dimethyl-4-formulbutyronitrile (27 g) which was prepared by referential example 3(a) was dissolved in MeOH (100 mL) then it was added to $NaBH_4$ (16.3 g) at 0° C. and the mixture was stirred at room temperature for 2.5 h. The reaction mixture was poured into a saturated $NH_4OH$ solution (150 mL) and extracted with ethyl acetate (50 mL×3). The ethyl acetate layer was washed with brine and dried ($Na_2SO_4$), filtered, and concentrated. The object compound was obtained (27.5 g).

MS (m/e: 128 ($M^++1$), 110, 96, 69, 55 (BP). IR ($cm^{-1}$),: 3448, 2950, 2866, 2242, 1473.

$^1$H-NMR ($CDCl_3$): 0.90 (6H,s,$(CH_3)_2$), 1.69 (2H,t,$CH_2$), 2.34 (2H,t,$CH_2$), 2.35 (1H,bs,OH), 3.31 (2H,s,—$CH_2$—).

(c) Synthesis of 4-dimethyl-5-methoxy-valeronitrile

4-Hydroxymethyl-4-dimethyl-butyronitrile (27.5 g) which was prepared by referential example 3(b), was dissolved in THF (100 mL) then it was added 55% NaH (12.5 g) and $CH_3I$ (36.7 g) at 0° C. and the mixture was stirred at room temperature for 3 h. The reaction mixture was poured into ice water (300 mL), and extracted with ethyl acetate (50 mL×3). The ethyl acetate layer was washed with brine and dried ($Na_2SO_4$), filtered, and concentrated in vacuo. The resulting product was purified by silica gel column chromatography using EtOAc: n-hexane (5:1). The object compound was obtained (22 g).

IR ($cm^{-1}$),: 2950, 2866, 2242, 1737.

$^1$H-NMR ($CDCl_3$): 0.91 (6H,s,$(CH_3)_2$), 1.67 (2H,t,$CH_2$), 2.32 (2H,t,$CH_2$), 3.05 (2H,s,$CH_2$), 3.31 (3H,s,$OCH_3$).

(d) Synthesis of 4-dimethyl-5-methoxypentanoic acid

4-Dimethyl-5-methoxy-valeronitrile (22 g) which was prepared by referential example 3(c), was dissolved in EtOH (30 mL) then it was added 50% KOH (30 mL) and the mixture was refluxed for 4 h. The mixture was concentrated in vacuo, the resulting residue was added to $H_2O$ (20 mL) and it was treated with 10% HCl to adjust the pH to 4.0. The reaction mixture was extracted with ethyl acetate (50 mL×3). The ethyl acetate layer was washed with brine and dried ($Na_2SO_4$), filtered, and concentrated in vacuo. The object compound was obtained (22 g).

MS (m/e): 142 ($M^+$-18), 115 (BP), 96, 69. IR ($cm^{-1}$),: 2950, 1707, 1452, 1413, 1293.

$^1$H-NMR ($CDCl_3$): 0.89 (6H,s,$(CH_3)_2$, 1.63 (2H,t,$CH_2$), 2.34 (2H,t,$CH_2$).3.06 (2H,s,$CH_2$), 3.31 (3H,s,$OCH_3$), 11.30 (1H,bs,COOH).

EXAMPLE

Example 1

Synthesis of N-[(2R)-2-(1'-carboxymethyl)-3-(azulene-1-yl)propionyl]-L-phenylalanine N-methylamide (Compound 1)

(a) Synthesis of 3-(3'-azulene-1-yl)propionyl-(4S)-4-benzyl-2-oxazolidinone

Azulene-1-propionic acid (2.1 g) was dissolved in THF (25 mL), and to its solution was added $NEt_3$ (1.65 mL) and then slowly dropwise pivaloyl chloride (1.45 mL) at 0° C. and allowed to stir at room temperature for 2 h. In a separate flask, (S)-(−)-4-benzyl-2-oxazolidine (2.66 g) was dissolved in THF (20 mL) at −78° C., to its solution was added n-butyllithium in n-hexane (7.5 mL) and allowed to stir for 30 min. This solution was then added to above mixed anhydride at −78° C. over 5 min. The mixture was then allowed to stir for 1 h at room temperature. The reaction mixture was poured into a saturated $NH_4Cl$ solution (80 mL) and extracted with ethyl acetate, the ethyl acetate layer was washed with saturated $NaHCO_3$ and brine, dried ($Na_2SO_4$), filtered, and concentrated in vacuo. The resulting product was purified by silica gel column chromatography ($SiO_2$, 150 g) using EtOAc: n-hexane (3:1). The object compound was obtained as a blue crystal (3.37 g).

MP (° C.): 95~96. MS (m/e): 359 ($M^+$), 141 (BP). IR (KBr, $cm^-$),: 1776, 1689, 1383, 1350, 1290.

$^1$H-NMR ($CDCl_3$ ppm): $\delta$2.95 (2H,d,—$CH_2$), 3.30~3.60 (4H,m,—$(CH_2)_2$—), 4.11 (2H,s,—$CH_2$—), 4.60 (1H,bs,—CH), 7.00—8.50 (12H,m,aromatic).

(b) Synthesis of (4S)-4-benzyl-3-[(2'R)-2-[(tert-butoxycarbonyl)methyl]-3'-[(azulene-1-yl)propionyl]-2-oxazolidinone A 1.69M solution of n-butyllithium in n-hexane. (7.0 mL) was added to a solution of diisopropylamine 1.5 mL in THF (20 mL) at −78° C. After stirred for 30 min, the compound (3.37 g) which was prepared by example 1(a) was added, then tert-butylbromoacetate (5.21 mL) was added, and the reaction mixture was allowed to warm to −20° C. After being stirred for 20 min, the reaction mixture was poured into a saturated $NH_4Cl$ solution (30 mL) and extracted with ethyl acetate (20 mL×3), the ethyl acetate layer was washed with brine, dried ($Na_2SO_4$), filtered, and concentrated in vacuo. The resulting product was purified by silica gel column chromatography ($SiO_2$, 150 g) using EtOAc: n-hexane (1:5). The object compound was obtained as a blue crystal (2.8 g).

MP(° C.): 146~148. MS (m/e): 474 ($M^++1$), 141 (BP). IR (KBr,$cm^{-1}$),: 1770, 1710, 1360, 1160.

$^1$H-NMR ($CDCl_3$): 1.38 (9H,s,tBu-), 2.80 (2H,d,—$CH_2$—), 2.95 (2H,d,—$CH_2$—), 2.90~3.50 (2H,m,—$CH_2$—), 3.85 (2H,d,—$CH_2$—), 4.38 (1H,bs,—CH), 4.65 (1H,bs,—CH), 7.00~8.50 (12H,m,aromatic).

(c) Synthesis of 3-(azulene-1-yl)-(2R)-2-[(tert-butoxycarbonyl)methyl]-propionic acid The compound (2.8 g) which was prepared by example 1(b) was dissolved in THF (20 mL) and H$_2$O (10 mL), and it was cooled to 0° C. 30% H$_2$O$_2$ (2.7 g) was slowly added to it, and the mixture was stirred. After 10 min, LiOH.H$_2$O (0.5 g) was added to it, and the mixture was stirred for 1 h at room temperature, then 10% Na$_2$SO$_3$ (20 mL) was added to the reaction mixture. After stirring 20 min, the solvent was concentrated in vacuo. The resulting residue was treated with saturated NaHCO$_3$ to adjust the pH to 8. The reaction mixture was extracted with ethyl acetate (20 mL×3), the ethyl acetate layer was washed with brine, dried (Na$_2$SO$_4$), filtered, and concentrated in vacuo. Free benzyl oxazolidinone could be recrystallized and recycled for further use. The aqueous layer was acidified with 10% HCl to pH 2. The mixture was extracted with ethyl acetate (20 mL×3), the ethyl acetate layer was washed with brine, dried (Na$_2$SO$_4$), filtered, and concentrated in vacuo. The resulting produce was purified by silica gel column chromatography (SiO$_2$, 150 g) using EtOAc: n-hexane (1:3). The object compound was obtained as a blue crystal (1.5 g).

MP(° C.): 86~88. MS (m/e): 314 (M$^+$), 141 (BP).

$^1$H-NMR (CDCl$_3$): 1.40 (9H,s,t-Bu), 2.28~2.70 (2H,m,—CH$_2$—), 3.15~3.31 (2H,d,—CH$_2$—), 3.58 (1H,m,CH), 7.00~8.40 (7H,m,aromatic).

(d) Synthesis of N-4-(azulene-1-yl)-(2R)-2-[(tert-butoxycarbonyl)methyl)-butanoyl-L-phenylalanine N-methylamide The compound (500 mg) which was prepared by example 1(c) was dissolved in DMF (10), and then HOBt-H$_2$O (0.24 g) and N-ethylmorpholine (0.18 g) was added. The mixture was stirred at 0° C. for 30 min, then L-phenylalanine N-methylamide (0.28 g) and WSCDI (0.3 g) was added to the mixture. The mixture was stirred for 4 h at room temperature. The reaction mixture was poured into 10% Na$_2$CO$_3$ (20 mL), and extracted with ethyl acetate (20 mL×3), the ethyl acetate layer was washed with brine, dried (Na$_2$SO$_4$), filtered, and concentrated in vacuo. The resulting product was purified by silica gel column chromatography (SiO$_2$, 50 g) using EtOAc: n-hexane (1:3). The object compound was obtained as a blue crystal (650 mg).

MP(° C.): 143~145. MS (m/e): 475 (M$^+$1), 141 (BP). IR (cm$^{-1}$),: 3304, 1722, 1638, 1536, 1152.

$^1$H-NMR (CDCl$_3$): 1.40 (9H,s,tBu), 2.38 (3H,d,CH$_3$), 2.41~2.68 (2H,m,CH$_2$), 2.88~2.98 (2H,m,CH$_2$), 3.15 (2H,d,CH$_2$), 3.38 (1H,dd,CH), 4.45 (1H,t,CH), 5.11 (1H,bs,NH), 5.75 (1H,d,NH), 7.05~8.30 (12H,m,aromatic).

(e) Synthesis of N-[(2R)-2-[(1'-carboxymethyl)-3—(azulene-1-yl)propionyl]-L-phenylalanine N-methylamide The compound (650 mg) which was prepared by example 1(d) was dissolved in CH$_2$Cl$_2$ (5 mL), trifluoroacetic acid (2 mL) was added at 0° C. The mixture was stirred for 2 h at room temperature. The reaction mixture was poured into ice water (50 mL) and it was extracted with CHCl$_3$ (20 mL×3). The CHCl$_3$ layer was washed with brine, dried (Na$_2$SO$_4$), filtered, and concentrated in vacuo. The resulting product was purified by silica gel column chromatography (SiO$_2$, 50 g) using CHCl$_3$: MeOH (7:1). The object compound was obtained as a blue crystal (400 mg).

MP(° C.): 168~170. MS(m/e): 418 (M$^+$), 141 (BP). IR (KBr,cm$^{-1}$),: 3304, 1722, 1633, 1593, 1545.

$^1$H-NMR (CDCl$_3$,ppm): 2.40 (3H,d,CH$_3$), 2.71 (2H,d,CH$_2$), 2.90~3.00 (2H,m,=CH$_2$), 3.25 (2H,d,CH$_2$), 3.80~3.82 (1H,m,CH), 4.40~4.42 (1H,m,CH), 7.00~8.40 (12H,m, aromatic).

Example 2

Synthesis of N-[(2R)-2-(2'-hydroxyamino-2'-oxo-ethyl)-3-(azulene-1-yl) propionyl]-L-phenylalanine N-methylamide (Compound 31).

The compound (200 mg) which was prepared by example 1 was dissolved in DMF (10 mL), and HOBt.H$_2$O (73.0 mg), N-ethylmorpholine (54.9 mg) was added. The mixture was stirred at 0° C. for 30 min, then hydroxylammonium chloride (33.2 mg), NEt$_3$ (48.3 mg) and WSCDI (191.2 g) was added. The mixture was stirred at room temperature for 3 h. The reaction mixture was poured into saturated NH$_4$Cl (30 mL), and extracted with ethyl acetate (20 mL×3). The ethyl acetate layer was washed with brine, dried (Na$_2$So$_4$), filtered, and concentrated in vacuo. The resulting product was purified by silica gel column chromatography (SiO$_2$, 50 g) using CHCl$_3$: MeOH (5:1). The object compound was obtained as a white crystal (83 mg).

MP(° C.): 162~164. MS (m/e): 401 (M$^+$-32), 141 (BP). IR (KBr, cm$^{-1}$),: 3310, 1722, 1650, 1593, 1545.

$^1$H-NMR (CDCl$_3$): 2.25 (2H,d,CH$_2$), 2.52 (3H,d,CH$_3$), 2.90 (2H,d,CH$_2$), 3.01~3.18 (2H,m,CH$_2$), 3.25~3.35 (1H,m, CH), 4.45 (1H,t,CH), 7.10~8.50 (12H,m,aromatic).

Example 3

Synthesis of N-[(2R)-2—(1'-carboxymethyl)-4-[(4-methoxyphenyl)oxy]butyloyl]-L-phenylalanine N-methylamide (Compound 8)

(a) Synthesis of (4S)-4-benzyl-3-[[4'-(4-methoxyphenyl)oxy]butyloyl]-2—oxazolidinone 4-(4-Methoxyphenyl)oxybutanic acid (3.0 g) was dissolved in THF (50 mL), and to its solution was added NEt$_3$ ((2.4 mL) and then slowly dropwise pivaloyl chloride (2.1 mL) at 0° C. and allowed to stir at room temperature for 2 h. In a separate flask, (S)-(-)-4-benzyl-2—oxazolidine (3.7 g) was dissolved in THF (25 mL) at −78° C., its solution was added n-butyllithium in n-hexane (10 mL) and allowed to stir for 30 min. This solution was then added to above mixed anhydride at −78° C. over 5 min. The mixture was then allowed to stir for 1 h at room temperature. The reaction mixture was poured into a saturated NH$_4$Cl solution (80 mL) and extracted with ethyl acetate, the ethyl acetate layer was washed with saturated NaHCO$_3$ and brine, dried (Na$_2$SO$_4$), filtered, and concentrated in vacuo. The resulting product was purified by recrystallization from ethyl acetate. The object compound was obtained as a white crystal (4.0 g).

MP(° C.): 128~130. MS (m/e): 370 (M$^+$+1), 247, 193, 117, 91 (BP).

IR (cm$^{-1}$),: 3040, 2940, 1780, 1690, 1220.

$^1$H-NMR (CDCl$_3$): δ2.01~2.30 (2H,m,—CH$_2$—), 2.50~3.30 (4H,m,—CH$_2$—, —CH$_2$—), 3.70 (3H,s,—OCH$_3$—), 3.95 (2H,d,—CH$_2$—), 4.01–4.20 (2H,d,—CH$_2$—), 4.40~4.80 (1H,m,CH), 6.78 (4H,s,aromatic), 7.00~7.30 (5H,m,aromatic).

(b) Synthesis of (4S)-4-benzyl-3-[(2'R)-2'-(tert-butoxycarbonyl)-4'-[(4-methoxyphenyl)butyroyl]-2-oxozolidinone A 1.69M solution of n-butyllithium in n-hexane (8.1 mL) was added to a solution of diisopropylamine 1.8 mL in THF (40 mL) at −78° C. After being stirred for 30 min, the compound (4.0 g) which was prepared by example 3(a) was added, then tert-butylbromoacetate (5.2 mL) was added, and the reaction mixture was stirred for 30 min at −78° C., and warmed to −20° C. over 1 h , and then stirred for 1 h at 0° C. The reaction mixture was poured into a saturated NH$_4$Cl solution (30 mL) and extracted with ethyl acetate, the ethyl acetate layer was washed with saturated NaHCO$_3$, and brine, dried (Na$_2$SO$_4$), filtered, and concentrated in vacuo. The resulting product was purified by silica gel column chromatography using EtOAc: n-hexane (1:5). The object compound was obtained as a colorless oil (2.53 g).

MS (m/e): 484 (M$^+$+1), 304, 178, 124 (BP), 91, 57. IR (cm$^{-1}$),: 2968, 1776, 1695, 1470, 1350.

$^1$H-NMR (CDCl$_3$): δ1.44 (9H,s,tert-Bu), 2.10 (2H,d,—CH$_2$—), 2.81 (2H,d,—CH$_2$—), 2.94 (2H,d,—CH$_2$—), 3.72 (3H,s,—OCH$_3$), 3.88~3.95 (2H,m,—CH$_2$—), 4.01~4.10 (2H,m,—CH$_2$—), 4.44 (1H,brs,—CH—), 4.64 (1H,brs,—CH—), 6.80 (4H,s,aromatic), 7.21~7.38 (5H,m,aromatic).

(c) Synthesis of (2R)-2-(tert-butoxycarbonylmethyl)-4-[(4-methoxyphenyl)oxy]butanoic acid The compound (2.53g) which was prepared by example 3(b) was dissolved in THF/H$_2$O (4:1) (25 mL) and cooled to 0° C. Slowly, dropwise and with stirring, 30% H$_2$O$_2$ (2.2 mL) was added. After 10 min, LiOH.H$_2$O (0.43 g) was added and stirred for 1 h at room temperature, then 10% Na$_2$SO$_3$ (30 mL) was added dropwise. After stirring 15 min, the solvent was concentrated in vacuo. The resulting residue was treated with saturated NaHCO$_3$ to adjust the pH 10. The reaction mixture was extracted with CHCL$_3$ (20 mL×3). The CHCL$_3$ layer was washed with brine and dried (Na$_2$SO$_4$), filtered, and concentrated in vacuo. Free benzyl oxazolidinone could be recrystallized and recycled for further use. The basic layer was then cooled and acidified with 10% HCl to pH 2. The mixture was extracted with ethyl acetate (20 mL×3), the ethyl acetate phase was washed with brine, dried (Na$_2$SO$_4$), filtered, and concentrated in vacuo. The resulting product was purified by silica gel column chromatography using EtOAc: n-hexane (1:3). The object compound was obtained (1.13 g) as a white crystal. MP(° C.): 92~94. MS (m/e): 324 (M$^+$), 233, 124 (BP), 84, 55.

IR (cm$^{-1}$),: 2968, 1731, 1509, 1470, 1443, 1371.

$^1$H-NMR (CDCl$_3$): δ1.45 (9H,s,tBu), 2.10 (2H,d,—CH$_2$—), 2.60 (2H,d,—CH$_2$—), 3.08 (1H,brs,—CH—), 3.78 (3H,s,—OCH$_3$), 4.00 (2H,t,—CH$_2$—), 6.70 (4H,s, aromatic).

(d) Synthesis of N-[(2R)-2—(tert-butoxycarbonylmethyl)-4-[(4-methoxyphenyl)oxy]butanoyl-L-phenylalanine N-methylamide The compound (500 mg) which was prepared by example 3(c) was dissolved in THF/DMF (3:1)(8 mL), L-phenylalanine N-methylamide (329 mg), DEPC (293 mg), Et$_3$N (182 mg) was added at 0° C. The mixture was stirred at room temperature for 3.5 h. The reaction mixture was poured into 10% Na$_2$CO$_3$ (20 mL), and extracted with ethyl acetate (20mL×3), the ethyl acetate layer was washed with brine, dried (Na$_2$SO$_4$), filtered, and concentrated in vacuo. The resulting product was purified by silica gel column chromatography using EtOAc: N-hexane (1:3). The object compound was obtained as a white crystal (0.64 g).

MP(° C.): 105~107. MS (m/e): 485 (M$^+$+1), 412, 361, 305, 120 (BP), 91, 58. IR (cm$^{-1}$),: 3292, 1728, 1641, 1548, 1509, 1233.

$^1$H-NMR (CDCl$_3$): δ1.42 (9H,s,t-Bu), 1.70~2.00 (4H,m,—CH$_2$—), 2.52 (2H,dd,—CH$_2$—), 2.52 (3H,d,—CH$_3$), 3.05 (1H,m,—CH—), 3.72 (3H,s,—OCH$_3$), 3.85 (2H,d,—CH$_2$—), 4.50 (1H,m,—CH—), 5.90 (1H,br,s), 6.40 (1H,br, s), 6.70~7.30 (9H,m,aromatic).

(e) Synthesis of N-[(2R)-2-[(1'-carboxymethyl)-4-[(4-methoxyphenyl)oxy]butanoyl]-L-phenylalanine N-methylamide The compound (600 mg) which was prepared by example 3(d) was dissolved in CH$_2$Cl$_2$ (10 mL), trifluoroacetic acid (3 mL) was added at 0° C. The mixture was stirred for 2 h at room temperature. The reaction mixture was poured into ice water (50 mL) and extracted with CHCl$_3$ (20mL×3). The CHCl$_3$ layer was washed with brine, dried (Na$_2$SO$_4$), filtered, and concentrated in vacuo. The resulting product was purified by recrystallization as ethyl acetate. The object compound was obtained as a white crystal (470 mg).

MP(° C.): 171~173. MS (m/e): 428 (M$^+$), 411, 288, 109 (BP), 55.

IR (cm$^{-1}$),: 3310, 2932, 1719, 1644, 1605, 1230.

$^1$H-NMR (CDCl$_3$): δ1.80~2.00 (4H,m,—CH$_2$—,—CH$_2$—), 2.45 (2H,dd, —CH$_2$), 2.58 (3H,s,—CH$_3$), 3.05 (2H,d,—CH$_2$), 3.75 (3H,s,—OCH$_3$), 4.50 (1H,t,—CH—), 6.70~7.30 (9H,m,aromatic).

Example 4

Synthesis of N-[(2R)-2-[2'-(5-methyl-2—oxo-1,3-dioxolen-4-yl)methylene-oxy-2'-oxo-ethyl]-5-[(4-methoxyphenyl)oxy]pentanoyl]-L-phenylalanine N-methylamide (Compound 61)

The compound (51 mg) which was prepared by example 3 was dissolved in DMF (2 mL), K$_2$CO$_3$ (18 mg) and 4-bromomethyl-5-methyl-2-oxo-1,3-dioxol (31 mg) was added at 0° C. The mixture was stirred at 0° C. for 1 h. The reaction mixture was poured into saturated NH$_4$Cl (30 mL) and extracted with ethyl acetate (20mL×3). The ethyl acetate layer was washed with brine, dried (Na$_2$SO$_4$), filtered, and concentrated in vacuo. The resulting product was purified by silica gel column chromatography using EtOAc: n-hexane (1:1). The object compound was obtained as a white crystal (45 mg).

MP(° C.): 98~100. MS (m/e): 555 (M$^+$), 424,301, 242, 162, 124, 69 (BP). IR (cm$^{-1}$), 3418, 1821, 1740, 1638, 1545, 1509, 1392, 1233, 1155, 699.

$^1$H-NMR (CDCl$_3$): δ1.57~1.82 (4H,m,—CH$_2$—, —CH$_2$—), 2.15 (3H,s,—CH$_3$), 2.47 (1H,d,—CH—), 2.67 (3H,d,—CH$_3$), 2.70~2.88 (2H,m,—CH$_2$—), 2.99 (1H,dd,—CH—), 3.16 (1H,dd,—CH—), 3.76 (3H,s,—OCH$_3$—), 3.86 (1H,m,—CH—), 3,92 (1H,m,—CH—), 4.57 (1H,q,—CH—), 4.74 (1H,ABq,—CH—), 4.84 (1H,ABq,—CH—), 5.66 (1H,d,—NH—), 6.45 (1H,d,—NH—), 6.74 (2H,d, aromatic), 6.81 (2H,d, aromatic, 7.23~7.32 (5H,m, aromatic).

Example 5

Synthesis of (2S)-2-[(2R)-2—(1'-carboxymethyl)-5-[(4-methoxyphenyl)oxy]pentanoyl]amino-3—(4-methoxy) phenylpropanoylmethylamide (Compound 18)

(a) Synthesis of N-[(2R)-2-(tert-butoxycarboxylmethyl)-5-(4-methoxyphenyl)oxy]pentanoyl]amino-3—(4-methoxy) phenylpropanoylmethylamide (2R)-2-(tert-butoxycarboxylmethyl)-5-(4-methoxyphenyl)oxy]pentanoic acid (250 mg) which was prepared by example 3 was dissolved in THF/DMF (3:1) (6 mL), 2(S)-2-amino-3—(4-methyl) phenylpropanoylmethylamide (250 mg), DEPC (140 mg) and Et$_3$N (90 mg) was added at 0° C. The reaction mixture was stirred at room temperature for 3.5 h. The reaction mixture was poured into 10% Na$_2$CO$_3$ (20 mL) and extracted with ethyl acetate (20mL×3). The ethyl acetate layer was washed with brine, dried (Na$_2$SO$_4$), filtered, and concentrated in vacuo. The resulting product was purified by silica gel column chromatography (Sio$_2$, 50 g) using EtOAc: n-hexane (2:1). The object compound was obtained as colorless oil (250 mg).

MS (m/e): 530 (M$^+$+2), 455, 332, 264, 124 (BP). IR (cm$^{-1}$),: 3286, 2920, 1722, 1644 1557.

$^1$H-NMR (CDCl$_3$): δ1.40 (9H,s,tBu), 1.50~1.80 (4H,m,—(CH$_2$)$_2$—), 2.50 (2H,d,CH$_2$), 2.68 (3H,d,—CH$_3$), 3.10 (2H, d,CH$_2$), 3.76 (3H,s,OCH$_3$), 3.78 (3H,s,OCH$_3$), 3.65~3.78 (1H,m,CH), 3.80~3.90 (2H,m,CH$_2$, 4.50 (1H,t,CH), 6.60~7.20 (8H,m,aromatic).

(b) Synthesis of (2S)-2-[(2R)-2-(1'-carboxymethyl) -5-(4-methoxyphenyl)oxy)pentanoyl]amino-3—(4-methoxy) -phenylpropanoyl methylamide.

The compound (250 mg) which was prepared by example 5(a) was dissolved in $CH_2Cl_2$ (4 mL), and trifluoroacetic acid (1.5 mL) was added at 0° C. The mixture was stirred for 2 h at room temperature. The reaction mixture was poured into ice water (30 mL) and extracted with $CHCl_3$ (20mL×3). The $CHCl_3$ layer was washed with brine, dried ($Na_2SO_4$), filtered, and concentrated in vacuo. The resulting product was purified by recrystallization as 50% EtOH. The object compound was obtained as white crystal (175 mg).

MP(° C.): 189~191. MS (m/e): 454 ($M^+$-18), 331, 263, 121, (BP), 69. IR ($cm^1$),: 3304,3100, 1722, 1641, 1545.

$^1$H-NMR ($CDCl_3$): δ1.55~1.80 (4H,m,—($CH_2$)$_2$—), 2.50 (2H,d,—$CH_2$—), 2.68 (3H,d,—$CH_3$), 3.00 (2H,d,$CH_2$), 3.70~3.75 (1H,d,—CH), 3.76 (3H,s,—$OCH_3$), 3.77 (3H, s,—$OCH_3$), 3.75~3.90 (2H,m,—$CH_2$), 4.45 (1H,t,CH), 6.75~7.20 (8H,m,aromatic).

Example 6

Synthesis of (2S)-2-[(2R)-2-(2'-hydroxyamino)-2'-oxo-ethyl)-5-[(4-methoxyphenyl)oxy]pentanoyl] amino-3-(4-methoxy)phenylpropanoylmethylamide (Compound 48)

The compound (125 mg) which was prepared by example 5(b) was dissolved in THF/DMF (3:1) (5 mL), hydroxylammonium chloride (25 mg), DEPC (61 mg) and $Et_3N$ (72 mg) were added at 0° C. The mixture was stirred at room temperature for 3.5 h. The reaction mixture was poured into 10% $Na_2CO_3$ (10 mL) and extracted with ethyl acetate (20mL×3). The ethyl acetate layer was washed with brine, dried ($Na_2SO_4$), filtered, and concentrated in vacuo. The resulting product was purified by silica gel column chromatography ($SiO_2$, 50 g) using $CHCl_3$: MeOH (5:1). The object compound was obtained as white crystal (62 mg).

MP(° C.): 135~137. MS (m/e): 455 ($M^+$-32), 332, 263, 191, 121 (BP).

$^1$H-NMR ($CDCl_3$): δ1.55~1.80 (4H,m,—($CH_2$)$_2$—), 2.20 (2H,d,$CH_2$), 2.68 (3H,d,—$CH_3$), 3.00 (2H,d,$CH_2$), 3.60~3.70 (2H,m,$CH_2$), 3.75 (6H,s,—$OCH_3$, —$OCH_3$), 3.85 (1H,t,CH), 6.70~7.20 (8H,m,aromatic).

Example 7

Synthesis of 2-[[N-(2R)-2-[1'-carboxymethyl)-5-[(4-methoxyphenyl)oxy]pentanoyl]-L-phenylalanyl]-aminoethanesulfonamide (Compound 12)

(a) Synthesis of 2-([N-(2R)-2-(1'-tert-butoxycarboyxlmethyl) -5-[(4-methoxyphenyl)oxy) pentanoyl]-L-phenylalanyl]amino-sulfonamide The compound (500 mg) which was prepared by example 3(c) was dissolved in $CH_2Cl_2$/DMF (4:1)(5 ML), HOBt (271 mg), WSCDI (339 mg) and N-methylmorpholine (0.19 mL) were added at 0° C. The mixture was stirred at room temperature for 1 h, 2-amino-ethanesulfonamide (481 mg) and N-methylmorpholine (0.19 mL) were added to the mixture. The reaction mixture was stirred for 3 h at room temperature. The reaction mixture was poured into ice water (50 mL) and extracted with ethyl acetate (20mL×3). The ethyl acetate layer was washed with brine, dried ($Na_2SO_4$), filtered, and concentrated in vacuo. The resulting product was purified by silica gel column chromatography ($SiO_2$, 50 g) using $CHCl_3$: MeOH (5:1). The object compound was obtained.

MS (m/e): 517 ($M^+$-75), 468, 412, 242, 163, 120,59 (BP). IR (KBr, $cm^{-1}$),: 3292, 2920, 1728, 1632, 1509, 1368,1341, 1233, 1146, 822, 747, 699.

$^1$H-NMR ($CDCl_3$): δ1.43 (9H,s), 1.54~1.71 (4H,m), 2.42 (2H,dd,J =16.1, 3.9 Hz), 2.55 (1H,m), 2.62 (1H,m), 3.16 (2H,d,J =7.3 Hz), 3.25 (2H,d,J=5.9 Hz), 3.61 (2H,q,J =5.9 Hz), 3.76 (3H,s), 3.82 (1H,m), 3.86 (1H,m), 4.54 (1H,q,J =7.1 Hz), 5.20 (2H,s), 6.48 (1H,d,J=7.3 Hz), 6.73~6.83 (4H,m), 7.14 (1H,t,J=5.9 Hz), 7.22~7.32 (5H,m)

(b) Synthesis of 2-[[N-(2R)-2-(1'-carboyxlmethyl)-5-[(4-methoxyphenyl)oxy]pentanoyl]-L-phenylalanyl]aminoethanesulfonamide The compound (886 mg) which was prepared by example 7(a) was dissolved in $CH_2cl_2$ (6 mL), trifluoroacetic acid (1 mL) was added at 0° C. The mixture was stirred for 3 h at room temperature. The reaction mixture was concentrated in vacuo. The object compound was obtained as a crystal (54%).

MS (m/e): 394 ($M^+$-142), 264, 163, 120 (BP). IR (KBr, $cm^{-1}$),: 3322, 2938, 1701, 1632, 1512, 1338, 1236, 1143, 1038, 741.

$^1$H-NMR (DMSO): δ1.61~1.69 (4H,m), 2.32 (1H,dd,J= 16.2, 6.4 Hz), 2.47 (1H,dd,J=16.2,7.6 Hz), 2.77 (1H,m), 2.95 (1H,dd,J=13.7, 8.8 Hz), 3.06~3.20 (3H,m), 3.56 (2H, m), 3.80 (3H,s), 3.92 (2H,t,J=5.9 Hz), 4.52 (1H,dd,J=14.2, 8.3 Hz), 6.92~7.39 (11H,m), 8.15 (1H,t,J=5.7 Hz), 8.29 (1H,d,J=7.8 Hz), 12.24 (1H,br,s).

Example 8

Synthesis of 2-[N-[(2R)-2-(2'-hydroxyamino-2'-oxo-ethyl)-5-[4-methoxyphenyl)oxy]pentanoyl]-L-phenylalanyl]amino-ethanesulfonamide (Compound 42).

The compound (363 mg) which was prepared by Example 7 was dissolved in $CH_2CL_2$/DMF (1:1)(4 mL), HOBt (125 mg), WSCDI (156 mg) and N-methylmorphiline (89 μg) were added at 0° C. After being stirred for 1 h, N-methylmorphiline (0.11 mL) and hydroxylammonium chloride (70 mL) were added at 0° C. and stirred overnight at room temperature. Saturated $NaHCO_3$ and ether were poured into the reaction mixture. The resulting precipitate was collected by filtration. The object compound was obtained (43%). MS(m/e): 394($M^+$-157), 263, 156, 124, 69 (BP). IR (KBR,$cm^{-1}$),: 3322, 2932, 1644, 1530, 1512, 1320, 1233, 1140, 1036, 814, 700.

$^1$H-NMR (DMSO): δ1.55~1.60 (4H,m), 2.09 (1H,dd,J= 14.7,7.3 Hz), 2.18(1H, dd, J=14.2, 6.4 Hz), 2.73 (1H,m), 2.95(1H,m), 3.12~3.15 (3H,m), 3.57 (2H,m), 3.80 (3H,s), 3.88 (2H,m), 4.50 (1H,s), 6.95~7.37 (9H,m), 8.26 (1H,m), 8.30 (1H,d,J=8.3 Hz), 8.90 (1H,br, s), 10.55 (1H,br,s)

Example 9

Synthesis of N-[(2R)-2-(1'-carboxymethyl)-4,4-dimethyl-5-methoxy-pentanoyl]-L-phenylalanine N-methylamide (Compound 28)

(a) Synthesis of 3-(4-dimethyl-5-methoxypentanoyl)-(4S)-4-benzyl-2-oxazolidine.

4-Dimethyl-5-methoxy-pentanoic acid (16.0 g) which was prepared by referential example 3 (d) was dissolved in THF (150 mL), and to its solution was added $NEt_3$ (12 mL) and then slowly dropwise pivaloyl chloride (14.5 mL) at 0° C. and allowed to stir at room temperature for 2 h. In a separate flask, (S)-(−)-4-benzyl-2-oxazolidine (26.6 g) was dissolved in THF (150 mL) at −78° C., to its solution was added n-butyllithium in n-hexane (75 mL) and allowed to stir for 30 min. This solution was then added to above mixed anhydride at −78° C. over 5 min. The mixture was then allowed to stir for 1 h at room temperature. The reaction mixture was poured into a saturated $NH_4Cl$ solution (150 mL) and extracted with ethyl acetate (50mL×3), the ethyl acetate layer was washed with saturated NaHCO₃ and brine, dried (Na₂SO₄), filtered, and concentrated in vacuo. The resulting product was purified by silica gel column chromatography using EtOAc:n-hexane (5:1). The object compound was obtained as a colorless oil (18.9 g).

MS (m/e): 319(M⁺), 174, 178, 55 (BP). IR (cm⁻¹),: 2950, 2866, 1782, 1734, 1695.

¹H-NMR (CDCl₃): δ0.93 (6H,s,—(CH₃)₂), 1.65~1.70 (2H,m, —CH₂), 2.70~2.80 (2H,m,—CH₂), 2.90~3.00 (2H, m,—CH₂—), 3.10 (2H,s,—CH₂_), 3.33 (3H,s,—OCH₃), 4.10~4.25 (2H,m,—CH₂), 4.60~4.70 (1H,m—CH), 7.10~7.40 (5H,m,aromatic), (b) Synthesis of (4S)-4-benzyl-3-[(2R)-2-(tert-butoxycarboxylmethyl)-4-dimethyl-5-methoxypentanoyl)-2-oxazolidinone.

The compound (11.5 g) which was prepared by example 9(a) was dissolved in THF (100 mL), and then 2.0M lithium diisopropylamide (LDA) in hexane (19.5 mL) was added at −78° C. After stirring for 1 h at −78° C., tert-butylbromoacetate (26 mL) was added dropwise. After stirring for 1 h the mixture was poured into a saturated NH₄Cl solution (150 mL). The mixture was extracted with ethyl acetate (150 mL), the organic layer was washed with brine, dried (Na₂SO₄), filtered, and concentrated in vacuo. The resulting product was purified by silica gel column chromatography using EtOAc:n-hexane (1:5). The object compound was obtained as a yellow crystal (10.8 g).

MP (° C.): 53. MS (m/e): 433 (M⁺), 320, 178, 143 (BP). IR (KBr,cm⁻¹),: 3300, 1800, 1750, 1400.

¹H-NMR (CDCl₃): δ0.89 (6H,d,—(CH₃)₂), 1.24~1.27 (2H,m,—CH₂), 1.44 (9H,s,tBu), 2.25 (2H,d,—CH₂), 2.60~2.78 (2H,m,—CH₂), 3.00~3.10 (2H,m,—CH₂), 3.21 (3H,s,—OCH₃), 4.10~4.20 (2H,m,—CH₂), 4.30 (1H,bs,—CH), 4.65 (1H,bs,—CH), 7.20~7.40 (5H,m,aromatic).

(c) Synthesis of (2R)-2-[(tert-butoxycarbonyl)methyl]-4-dimethyl-5-methoxypentanoic acid.

The compound (10.0g) which was prepared by example 9(b) was dissolved in THF (30 mL) and H₂O (10 mL), and cooled to 0° C. Slowly, dropwise and with stirring, 30% HO₂ (20 mL) was added. After 10 min., LiOH.H₂O (1.9 g) was added and stirred for 1 h at room temperature, then 10% Na₂SO₃ (40 mL) was added dropwise. After stirring 20 min, the solvent was concentrated in vacuo. The resulting residue was treated with saturated Na₂CO₃ to adjust the pH 10. The reaction mixture was extracted with ethyl acetate (20mL×3). The ethyl acetate layer was washed with brine and dried (Na₂SO₄), filtered, and concentrated in vacuo. Free benzyl oxazolidinone could be recrystallized and recycled for further use. The basic layer was then cooled and acidified with 10% HCl to pH2. The mixture was extracted with ethyl acetate (20mL×3). The ethyl acetate layer was washed with brine, dried (Na₂SO₄), filtered, and concentrated in vacuo. The resulting product was purified by silica gel column chromatography using EtOAc:n-hexane (1:3). The object compound was obtained as a colorless oil (4.0 g).

IR (KBr, cm⁻¹),: 2968, 1728, 1368, 1152.

¹H-NMR (CDCl₃): δ0.91 (6H, d,—(CH₃)₂), 1.43 (9H,s,tBu⁻), 1.80 (2H,d,—CH₂), 2.20 (2H,d,—CH₂), 2.86(1H, bs,—CH), 3.06 (2H,s—CH₂), 3.28 (3H,s,—OCH₃)

(d) Synthesis of N-[(2R)-2-(tert-butoxycarbonylmethyl)-4,4-dimethyl-5-methoxy]pentanoyl]-L-phenylalanine N-methylamide The compound (1.0 g) which was prepared by example 9(c) was dissolved in DMF 15 mL), L-phenylalanine N-methylamide (0.94 g) and NaHCO₃ (5.0 g) was added. The mixture was stirred at 0° C. for 30 min, then DPPA (1.5 g) was added at 0° C. The reaction mixture was stirred for 1 h at 0° C., warmed to room temperature over 8 h. The reaction mixture was poured into saturated NH₄Cl (50 mL), and extracted with ethyl acetate (30 mL×3), the ethyl acetate layer was washed with brine, dried (Na₂SO₄), filtered, and concentrated in vacuo. The resulting product was purified by silica gel column chromatography using EtOAc:n-hexane (3:1). The object compound was obtained as a colorless oil (0.9 g).

MS (m/e): 434(M'), 361, 161, 92 (BP). IR (KBr, cm⁻¹),: 3292, 2968, 1710, 1536.

¹H-NMR (CDCl₃): δ0.81 (6H,d,—(CH₃)₂), 1.20~1.30 (2H,m, —CH₂_), 1.43 (9H,s,tBu), 2.10 (2H,d,—CH₂), 2.50 (2H,d,—CH₂), 2.68 (3H,d,—CH₃), 2.96 (2H,s,—CH₂_), 3.00~3.15 (1H,m—CH), 3.20 (3H,s,—OCH₃), 4.55 (1H, q,—CH), 6.20 (1H,bs-NH), 6.60 (1H,d-NH), 7.10~7.40 (5H, m,aromatic).

(e) Synthesis of N-[(2R)-2-[(1'-carboxymethyl)-4,4-dimethyl-5-methoxypentanoyl]-L-phenylalanine N-methylamide The compound (600 mg) which was prepared by example 9(d) was dissolved in CH₂Cl₂ 5 (mL), trifluoroacetic acid (2 mL) was added at 0° C. The mixture was stirred at 3 h at room temperature. The reaction mixture was poured into saturated NH₄Cl (10 mL) and extracted with ethyl acetate (20 mL×3). The ethyl acetate layer was washed with brine, dried (Na₂SO₄), filtered, and concentrated in vacuo. The resulting product was purified by silica gel column chromatography using EtOAc. The object compound was obtained as a colorless oil (400 mg).

MS (m/e): 360 (M'-18), 302, 273, 163 (BP). IR (KBr, cm⁻¹),: 3292, 3070, 2926, 1707.

¹H-NMR (CDCl₃): δ0.84 (6H,d,—(CH₃)₂), 1.24~1.27 (2H,m—CH₂) 2.20 (2H,d,—CH₂), 2.68 (3H,d,—CH₃), 2.70 (2H,d,—CH₂), 2.85 (1H,bs—CH), 3.08(2H,s,—CH₂), 3.25 (3H,s—OCH₃), 4.65(1H,g-CH), 6.20(1H,bs-NH), 7.10~7.30(5H,m,aromatic).

$[\alpha]^D 25 = -5.80 (C=1, MeOH)$.

Example 10

Synthesis of N-[(2R)-2-(2'-hydroxyamino-2'-oxo-ethyl)-4-dimethyl-5-methoxy-pentanoyl]-L-phenylalanine N-methylamide (Compound 58).

(a) Synthesis of N-[(2R)-2-(2'-hydroxyamino-2'-oxo-ethyl)-4-[(4-dimethyl-5-methoxy-pentanoyl]-L-phenylalanine N-methylamide The compound (300 mg) which was prepared by example 9 was dissolved in DMF (20 mL), HOBt (144 mg) and N-ethylmorpholine (215 mg) were added. The mixture was stirred at 0° C. for 30 min, then o-benzhydroxyamine (152 mg) and WSCDI (179 g) was added. The mixture was stirred at room temperature for 3.5 h. The reaction mixture was poured into 10% Na₂CO₃ (30 mL), and extracted with ethyl acetate (20 mL×3). The ethyl acetate layer was washed with brine, dried (Na₂SO₄), filtered, and concentrated in vacuo. The resulting product was purified by silica gel column chromatography using EtOAc. The object compound was obtained as a colorless oil (380 mg).

IR (KBr,cm⁻¹),: 3293, 3058, 3022, 2944, 1734.

¹H-NMR (CDCl₃): δ0.82 (6H,d,—(CH₃)₂), 1.20~1.30 (2H,m,—CH₂—), 1.70~1.80 (2H,m,—CH₂), 2.20 (2H,d,—CH₂_), 2.65 (3H,d,—CH₃), 2.80 (1H,bs—CH), 3.05 (2H, s,—CH₂), 3.20 (3H,s,—OCH₃), 4.45 (1H,q—CH), 4.88 (2H,s,CH₂), 6.21 (1H,bs—NH), 6.88 (1H,d,-CN), 7.10~7.40 (1OH,m,aromatic).

(b) Synthesis of N-[(2R)-2-(2'-hydroxyamino-2-oxo-ethyl)-4-[(4-dimethyl-5-methoxy)pentanoyl]-L-phenylalanine N-methylamide A mixture of the compound (350 mg) which was prepared by example 10(a), and 5% Pd on carbon (5 mg) in MeOH (10 mL) was stirred for 2 h under a hydrogen atmosphere, filtered and concentrated. The resulting product was purified by silica gel column chromatography using $CHCl_3$:MeOH (7:1). The object compound was obtained as a white crystal (273 mg).

MP (° C.): 134~135. MS (m/e): 360 (M'-33), 302, 162, 84 (BP).

IR(KBr, cm-1),: 3310, 3028, 2920, 1656, 1536.

$^1$H-NMR ($CDCl_3$): δ0.61(2H,d,$CH_2$), 0.80 (6H,s,—($CH_3$)$_2$), 1.10~1.30 (2H,m,—$CH_2$), 2.01~2.10 (2H,m,—$CH_2$), 2.68 (3H,d,—$CH_3$), 3.05 (2H,s,$CH_2$), 3.05~3.15 (1H,m,—CH), 3.24 (3H,s,—$OCH_3$), 4.50 (1H,q—CH), 7.02 (1H,bs, NH), 7.15~7.40 (5H,m,aromatic) 7.70 (1H,d,NH).

$[\alpha]^D 25 = -10.80 (c=1, MeOH)$.

By similar techniques, the other compounds listed at pages 7–11 may be obtained. Melting point for these compounds are set forth in Table 2.

TABLE 2

| Comp. | MP (° C.) | Comp. | MP (° C.) | Comp. | MP (° C.) |
|---|---|---|---|---|---|
| 2 | 173~175 | 23 | 158~160 | 44 | 193~194 |
| 3 | 159~163 | 24 | 68~70 | 45 | 190~193 |
| 4 | 101~103 | 25 | 80~82 | 46 | 109~110 |
| 5 | 159~161 | 26 | 75~77 | 47 | 182~184 |
| 6 | 186~188 | 27 | 56~58 | 49 | 85~88 |
| 7 | 88~89 | 29 | 62~66 | 50 | 168~170 |
| 9 | 172~173 | 30 | 173~175 | 51 | 172~174 |
| 10 | 128~129 | 32 | 98~99 | 52 | 179~181 |
| 11 | 60~62 | 33 | 202~205 | 53 | 180~182 |
| 13 | 170~171 | 34 | 78~80 | 54 | 86~90 |
| 14 | 125~127 | 35 | 170~172 | 55 | 123~125 |
| 15 | 146~148 | 36 | 185~189 | 56 | 142~145 |
| 16 | 115~116 | 37 | 111~112 | 57 | 59~61 |
| 17 | 144~146 | 38 | 162~164 | 59 | 174~176 |
| 19 | 88~90 | 39 | 187~189 | 60 | 170~178 |
| 20 | 89~91 | 40 | 146~148 | 62 | 103~105 |
| 21 | 129~131 | 41 | 168~170 | 63 | 135~137 |
| 22 | 158~161 | 43 | 195~197 | 64 | 104~106 |

What is claimed is:

1. A method of treating a patient suffering from destruction of extra cellular matrix induced by matrix metalloproteinases comprising administering a matrix metalloproteinases inhibitory effective amount of a compound of the following formula (I) or a pharmaceutically acceptable salt thereof

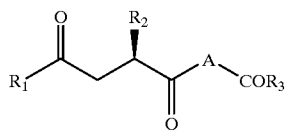
(I)

wherein $R_1$ represents

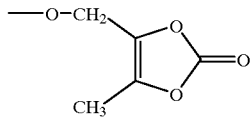

$R_2$ represents

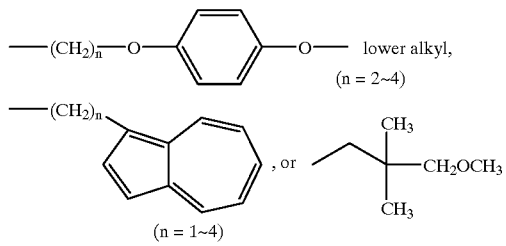

A represents

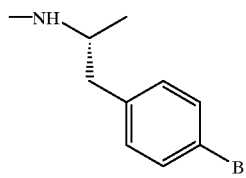

in which B is hydrogen, aryl, —o— lower alkyl,

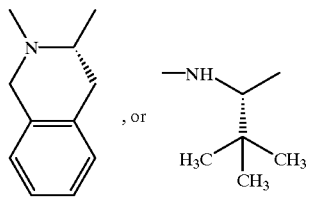

$R_3$ represents —$NHCH_3$, —NH—tBu, or

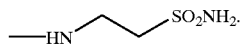

2. A pharmaceutical composition used to treat disease related to destruction of extra cellular matrix induced by matrix metalloproteinases, wherein an active ingredient is a compound of the general formula (I) or a salt thereof with a pharmaceutically acceptable base,

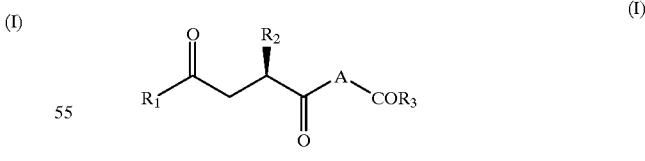
(I)

wherein $R_1$ represents

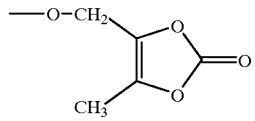

R₂ represents
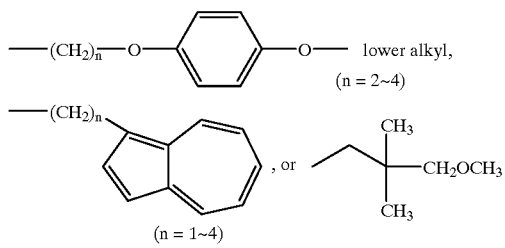
(n = 1~4)
A represents
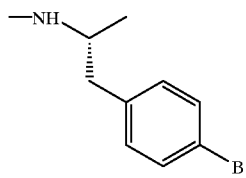
in which B is hydrogen, aryl —o— lower alkyl,
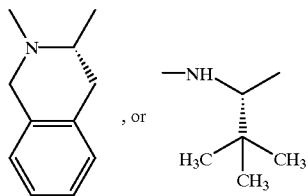, or
R₃ represents —NHCH₃, —NH—tBu, or
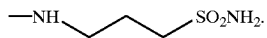.
3. A compound of general formula (I) or a pharmaceutically acceptable salt thereof,
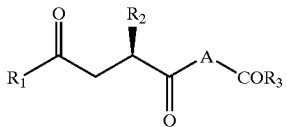 (I)
wherein R₁ represents
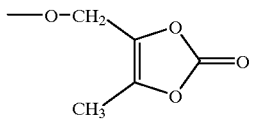
R₂ represents
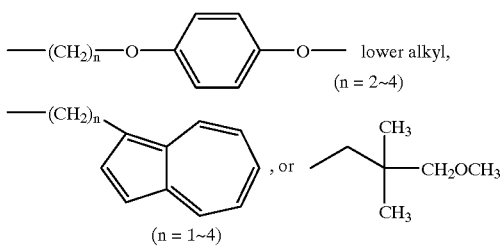
(n = 1~4)
A represents
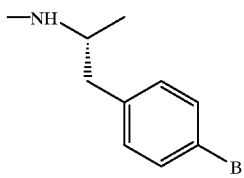
in which B is hydrogen, aryl, —o— lower alkyl,
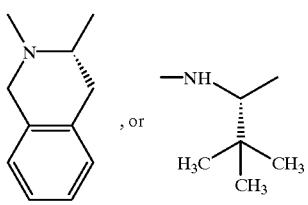, or
R₃ represents —NHCH₃, —NH—tBu, or
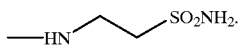.
* * * * *